(12) United States Patent
Dominik et al.

(10) Patent No.: US 8,894,648 B2
(45) Date of Patent: Nov. 25, 2014

(54) SURGICAL CLAMPING DEVICE

(75) Inventors: Robert Dominik, Commughy (CH); This Aebi, Grenchen (CH)

(73) Assignee: Stryker Trauma SA (CH)

( * ) Notice: Subject to any disclaimer, the term of this patent is extended or adjusted under 35 U.S.C. 154(b) by 274 days.

(21) Appl. No.: 13/392,157

(22) PCT Filed: Aug. 28, 2009

(86) PCT No.: PCT/EP2009/006265
§ 371 (c)(1),
(2), (4) Date: Jul. 10, 2012

(87) PCT Pub. No.: WO2011/023212
PCT Pub. Date: Mar. 3, 2011

(65) Prior Publication Data
US 2012/0271308 A1  Oct. 25, 2012

(51) Int. Cl.
A61F 5/04 (2006.01)
A61B 17/70 (2006.01)
A61B 17/66 (2006.01)
A61B 17/60 (2006.01)

(52) U.S. Cl.
CPC .............. *A61B 17/7077* (2013.01); *A61B 17/66* (2013.01); *A61B 17/708* (2013.01); *A61B 2017/606* (2013.01)
USPC ........................................................ 606/57

(58) Field of Classification Search
CPC .. A61B 17/7077; A61B 17/708; A61B 17/66; A61B 2017/606
USPC ........................................................ 606/57
See application file for complete search history.

(56) References Cited

U.S. PATENT DOCUMENTS

| 3,807,889 | A | * | 4/1974 | Kiezel ............................. 408/108 |
| 5,152,778 | A | * | 10/1992 | Bales et al. .................... 606/205 |
| 8,465,529 | B2 | * | 6/2013 | Choi et al. ..................... 606/279 |
| 2004/0138659 | A1 | | 7/2004 | Austin et al. |
| 2006/0200132 | A1 | | 9/2006 | Chao et al. |
| 2008/0294206 | A1 | * | 11/2008 | Choi et al. ................... 606/86 A |
| 2009/0062858 | A1 | * | 3/2009 | Dziedzic et al. .............. 606/278 |
| 2013/0245694 | A1 | * | 9/2013 | Choi et al. .................... 606/279 |

FOREIGN PATENT DOCUMENTS

DE  8712943 U1  11/1987

OTHER PUBLICATIONS

International Search Report, PCT/EP2009/006265, dated May 3, 2010.

* cited by examiner

*Primary Examiner* — Ellen C Hammond
(74) *Attorney, Agent, or Firm* — Lerner, David, Littenberg, Krumholz & Mentlik, LLP

(57) ABSTRACT

A surgical clamping device is provided for receiving distal ends of handles having bone attachment members disposed thereon in a recess disposed in the surgical clamping device. When an adjustment mechanism is in a first state, the distal ends of the handles are able to pivot and, optionally, to move axially within the recess of the surgical clamping device. When the adjustment mechanism is placed into a second state by adjusting the adjusting mechanism, the surgical clamping device applies a clamping force to the distal ends of the handles such that they are fixed within the recess of the surgical clamping device.

19 Claims, 12 Drawing Sheets

SURGICAL CLAMPING DEVICE

CROSS-REFERENCE TO RELATED APPLICATION

The present application is a national phase entry under 35 U.S.C. §371 of International Application No. PCT/EP2009/006265 filed Aug. 28, 2009, published in English, incorporated herein by reference.

TECHNICAL FIELD

The present invention relates to a surgical clamping device for use in an orthopaedic procedure, and to a surgical assembly including the surgical clamping device, bone attachment member handles, and bone attachment members. The present invention also relates to a method of treating bone structures. More specifically, the surgical clamping device is in particular adapted for use in a dekyphosis procedure, a lordosis reduction procedure, or any other sagitall angulation reduction procedure.

BACKGROUND

In the field of treating spinal disorders (e.g., a surgery for realigning misaligned vertebrae), an operator implants one or several bone attachment members such as bone screws into the misaligned vertebrae, and re-aligns the vertebrae using handles attached to the bone attachment members.

A distance between the bone attachment members can be set by a distractor device disposed between distal ends of the bone attachment members. The distractor device is adjusted to increase or decrease the distance between the bone attachment members to aid the operator in adjusting the positioning of the vertebrae. Distal ends of the handles may be contained within a linkage element adapted to stabilize the distal handle ends during distraction (or compression) while allowing the operator to manipulate the positioning of the handles with the bone attachment members by pivotal and/or rotational movement.

German utility model G 87 12 943 describes a surgical assembly having bone attachment members disposed on handles and a distractor device disposed near proximal ends of the handles. Distal ends of the handles can be inserted into holes in an elongated linkage element such that the linkage element is disposed around the distal ends. Several holes are located along the linkage element, so that the operator can choose the desired distance between the two handles by inserting the distal handle ends of the handles into the holes having a desired separation distance. The handles are pivotable and rotatable within the holes of the linkage element.

U.S. patent application No. 2009/0062858 describes a further surgical assembly having bone attachment members disposed on proximal ends of two handles, a distractor device and a linkage element receiving distal ball ends of the handles. The linkage element comprises two ball cups for receiving the distal ball ends of the handles such that the handles may be pivoted and rotated. Additionally, one of the ball cups may be moved axially along the linkage element so that an operator can change an axial distance between the distal ends of the handles.

In the surgical assemblies of the prior art, the operator positions the handles to obtain an approximated alignment of the vertebrae. The operator then checks the alignment of the vertebrae with the selected positioning of the bone attachment members by taking and analysing an X-ray image of the realigned vertebrae. Based on the X-ray image, the operator can confirm a proper alignment of the vertebrae, or may make further adjustments as necessary.

Because X-ray exposure is a known health risk, and because an operator may have to take X-ray images frequently during the realignment procedure and during successive procedures, the operator desires to leave the operating room when the X-ray images are taken. However, because the surgical assemblies of the prior art are designed to allow the operator to manipulate the handles by pivoting or rotating movements, the positioning of the assembly is potentially unstable. Therefore, the operator may be reluctant to release his grip on the handles in order to be able to leave the room during the X-ray imaging procedure.

Further, when the operator releases his grip on the handles, the surgical assembly may move, requiring the operator to reposition the assembly. This may be time consuming and inefficient for the operator, and may cause additional damage to body tissue and pain for the patient. Still further, the additional time consumed in readjusting the assembly that has moved when the operator releases his grip may cause a lengthened surgery time, thus causing an increased health risk to the patient.

SUMMARY

It is therefore an object to provide a surgical clamping device that facilitates maintaining a positioning of bone attachment members such that an operator may release his grip on handles of the surgical clamping device, and may leave a surgical area, for example when X-ray images are being taken or in other circumstances. It is also an object to provide a surgical assembly comprising the surgical clamping device, the handles, and the bone attachment members. It is a further object to provide a method of treating bone structures (such as aligning vertebrae, in which alignment of the vertebrae can be maintained when the operator releases his grip).

In order to achieve these objects, a surgical clamping device provided, comprising at least one recess disposed therein and adapted to receive distal ends of a plurality of handles having bone attachment members disposed thereon, and an adjusting mechanism adapted to adjust the recess between a first state of the adjusting mechanism in which the distal end of at least one of the plurality of handles is pivotable within the recess and a second state of the adjusting mechanism in which the distal ends of the plurality of handles are axially and pivotally fixed in the recess of the surgical clamping device.

In the first state, the distal end of the at least one of the plurality of handles may further be at least one of rotatable and movable in an axial direction of the recess. Moreover, in the second state the distal ends of the plurality of handles may further be rotatably fixed in the recess such that the distal ends of the handles are completely prevented from a change in position.

In one variant, a dedicated recess is provided in the surgical clamping device for each distal handle end. In an alternative variant, the recess defines a single space in which two or more distal handle ends can be accommodated.

According to one implementation, the surgical clamping device may comprise a clamping mechanism. For example, the surgical clamping device may be comprised of two or more opposing clamping members. In one aspect, the clamping members may be symmetrically opposing members. In another aspect, at least one of the clamping members could be comprised of a plurality of parts or sections. The surgical clamping device may further, for example, be comprised of a single part comprising a hinge or a flexible portion adapted to be folded along the hinge or flexible portion such that the two sides of the clamping device disposed on either side of the hinge or flexible portion are disposed opposite to each other to form the opposing clamping members of the surgical clamping device.

One or more grooves may be disposed on one or more of the opposing clamping members (or on portions thereof). The grooves may form a part of the recess of the surgical clamping device. The distal ends of the plurality of handles may be supported by the grooves of the clamping members in the first state, such that the distal ends cannot be removed from the recess without widening a distance between the clamping members.

According to another aspect, when the adjusting mechanism is adjusted, the position of the adjusting mechanism may change in relation to an adjusting mechanism receiving portion disposed on the surgical clamping device, thereby changing a distance between the opposing clamping members (or on portions thereof). The adjusting mechanism may engage the adjusting mechanism receiving portion in a threaded or any other manner.

The adjusting mechanism may comprise a compression screw having a threaded portion and a handle member coupled to the compression screw. The adjusting mechanism may further comprise a rim located near the handle member and an elastic member located on a shaft of the compression screw between the rim and the threaded portion. The handle member may comprise a knob, which may be turned by the operator to adjust the compression screw.

Further, the adjusting mechanism receiving portion may comprise a threaded portion adapted to receive the threaded portion of the compression screw such that, when the adjusting mechanism is adjusted, the threaded portion of the adjusting mechanism receiving portion couples with the threaded portion of the compression screw to move the adjusting mechanism in relation to the adjusting mechanism receiving portion when the handle member is turned. Thereby, the distance between the clamping members may be changed.

The clamping members may be movable (e.g., pivotable) relative to each other. To this end, the adjusting mechanism receiving portion may comprise a tapered portion having a relatively large cross section on an outer side thereof that tapers down to a relatively smaller diameter (e.g., to the diameter of the threaded portion of the adjusting mechanism receiving portion). Thereby, a range of relative displacement (e.g., a pivoting) of the clamping members may be allowed such that a distance between the clamping members at one end is smaller than the distance between the members at an opposite end.

According to a still further aspect, the elastic member may be adapted to urge the two opposing clamping members toward each other. For example, the elastic member may be disposed between a surface of a clamping member and the rim of the adjusting mechanism.

Further, one or more coupling members may be disposed at least partially between the clamping members to axially and/or rotationally align the clamping members. The coupling members may further comprise spacer portions adapted to maintain a minimum space between the ends of the opposing clamping members (e.g., against the compression force of the elastic member). The coupling members may further be adapted to provide a minimum space between the ends of the opposing clamping members in order to facilitate the assembly of the distal ends of the handles within the surgical clamping assembly. Further, the coupling members may be disposed in coupling holes of the clamping members. The coupling holes may be elongated, thereby allowing a pivotal movement of the coupling members in the coupling holes (and allowing the coupling members to pivot relative to each other).

According to another aspect, a surgical assembly comprising at least one surgical clamping device and a plurality of handles having distal ends disposed in the at least one recess is provided. The handles may each comprise hand grips adapted to be gripped by an operator. Further, connecting members may be disposed between the handles and the bone attachment members.

The distal end of each handle may comprise a ball joint member adapted to pivot and, optionally, to move axially and/or rotate within the recess in the first state, and adapted to be fixed at least axially and pivotably by the surgical clamping device in the second state by a clamping or compressing force.

The surgical assembly comprising the surgical clamping device may also comprise a distractor adapted to fix the bone attachment members at a selected distance from each other at or near the point at which the distractor is attached, such that the operator is able to pivot the handles freely. The surgical assembly may be comprised of two surgical subassemblies, each comprising the handles, clamping members, bone attachment members, connector adaptors, and distractor.

According to a further aspect, a method of treating bone structures is provided, comprising positioning bone attachment members in a desired position, and adjusting an adjusting mechanism disposed on clamping members to urge the clamping members together such that distal ends of handles having the bone attachment members attached thereto and disposed in a recess located between the two clamping members are compressed between the clamping members. In this way, the handles are pivotably and axially fixed within the recesses.

The method may, for example, be employed to treat spinal disorders. More specifically, treatment of spinal disorders may comprise the alignment of vertebrae. In general, the method may be used in a dekyphosis procedure, a lordosis reduction procedure, or any other sagitall angulation reduction procedure.

BRIEF DESCRIPTION OF THE DRAWINGS

The foregoing objects, features, aspects and advantages will become more apparent from the following detailed description when taken in conjunction with the accompanying drawings.

DETAILED DESCRIPTION

Figure 1:
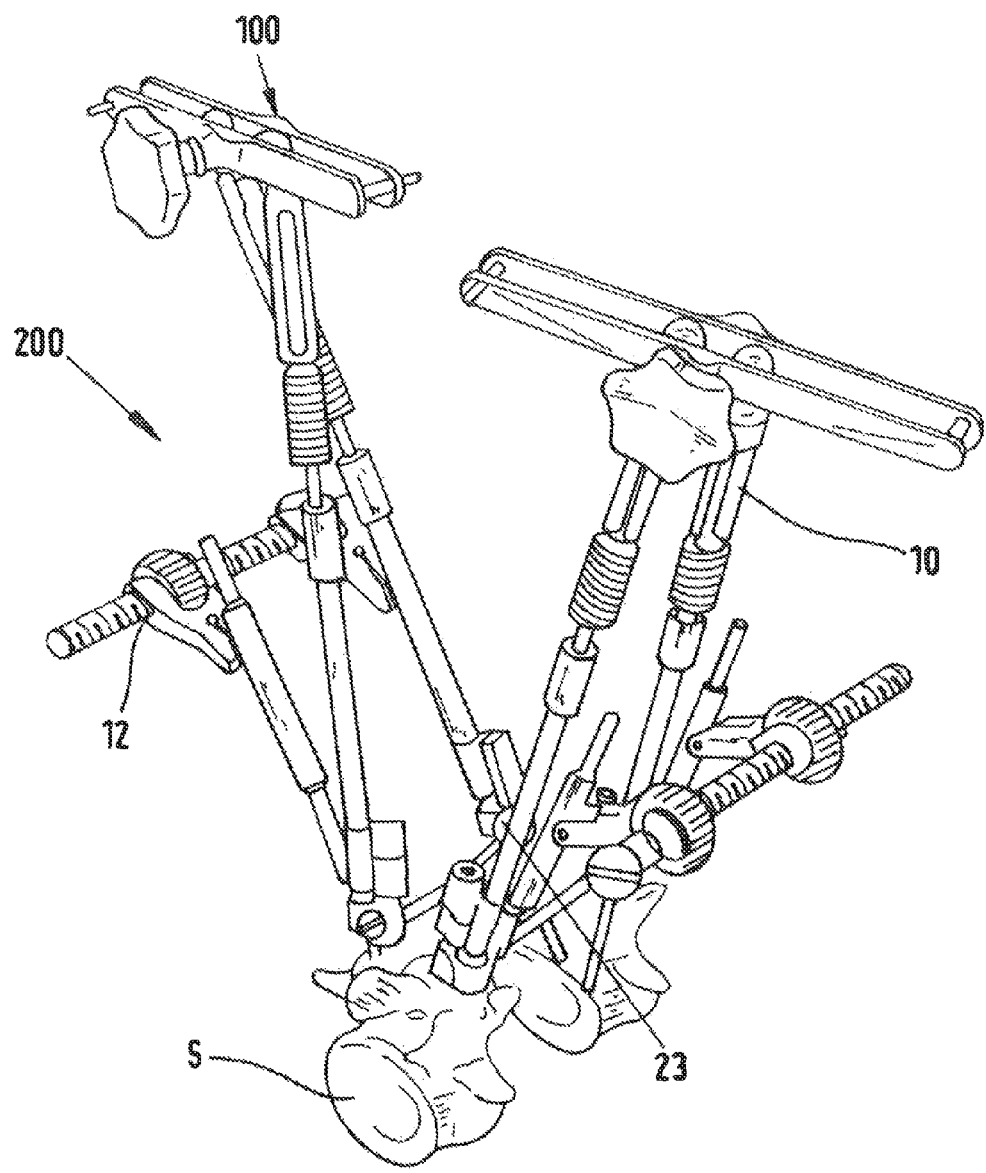
FIG. 1 is a perspective view showing an embodiment of a surgical assembly in an example procedure.

Hereinafter, embodiments of the surgical clamping device, surgical (sub-)assembly, and surgical method will be described with reference to the accompanying figures. The same reference numerals are used to refer to identical elements. In the following, the term "distal" refers to a direction away from a surgical site, and the term "proximal" refers to a direction toward the surgical site.

Figure 2:
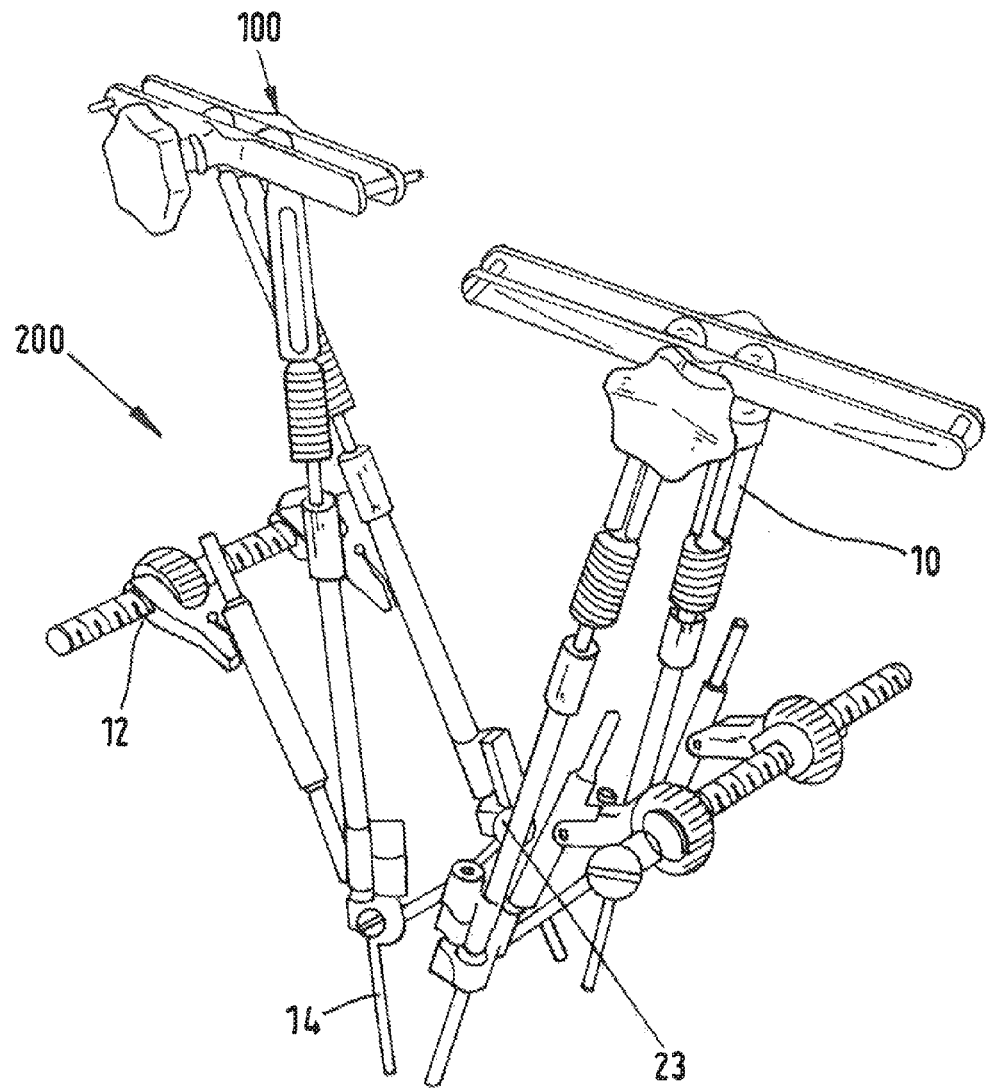
FIG. 2 is a perspective view of the surgical assembly of FIG. 1 showing bone attachment members.
Figure 3:
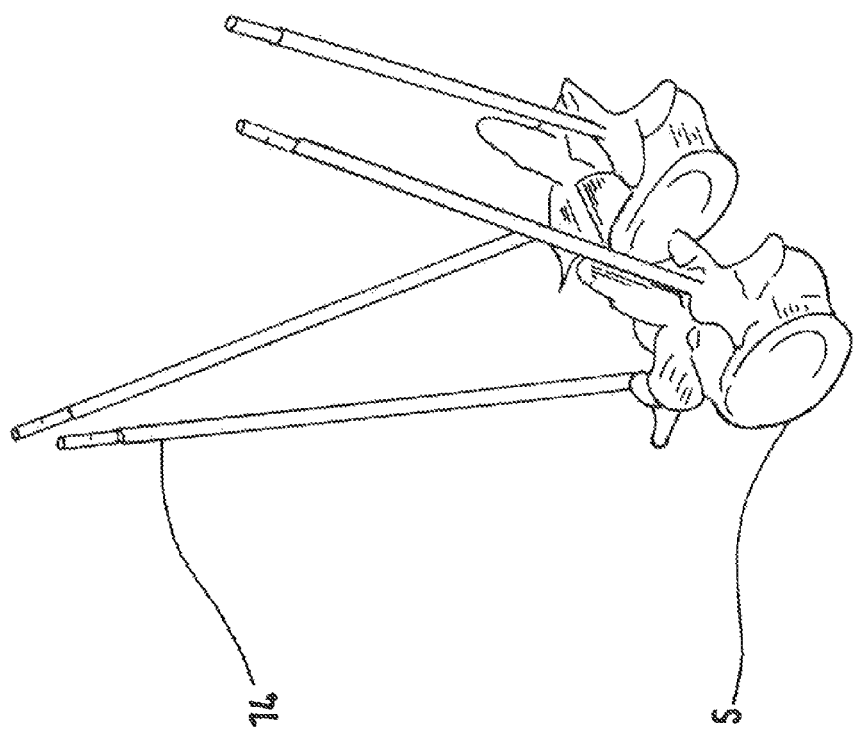
FIG. 3 is a perspective view showing an embodiment of the bone attachment members in the example procedure.

FIGS. 1 and 2 show a perspective view of a surgical assembly 200 comprising two surgical clamping devices 100, each having two handles 10, two connector adaptors 23, a distractor 12, and two bone attachment members 14. FIG. 1 shows a perspective view of the surgical assembly 200 having the attachment members 14 disposed in vertebrae S selected for realignment. FIG. 2 shows a perspective view of the surgical assembly 200 without the vertebrae S for the sake of illustration. In particular, FIG. 2 illustrates the orientation of the bone attachment members 14. FIG. 3 shows a detail view of the bone attachment members 14 disposed in the vertebrae S.

As illustrated in FIGS. 1 and 2, the bone attachment members 14 are disposed on proximal ends of the connector adaptors 23, and may be realized, for example, in the form of bone screws or bone pegs. More specifically, the bone attachment members 14 may be Schanz-type screws. The connector adaptors 23 are located on the proximal ends of the handles 10 to facilitate the connection of the bone attachment members 14 to the handles 10. Each distractor 12 is disposed near the proximal ends of the connector adaptors 23. For example, each distractor 12 may be positioned close to a point of attachment between the bone attachment members 14 and the connector adaptors 23, and can be used by the operator to set or adjust the distance between the bone attachment members 14, with the connector adaptors 23, bone attachment members 14, and handles 10 still able to pivot around the attachment points of the distractor 12.

The surgical clamping device 100 is able to be disposed in a first state, i.e., released state, in which at least one of the handles 10 is free to rotate, pivot and move axially within the surgical clamping device 100, and a second state, i.e., clamped state, in which the handles 10 are fixed rotationally axially and pivotably within the surgical clamping device 100

Figure 4:
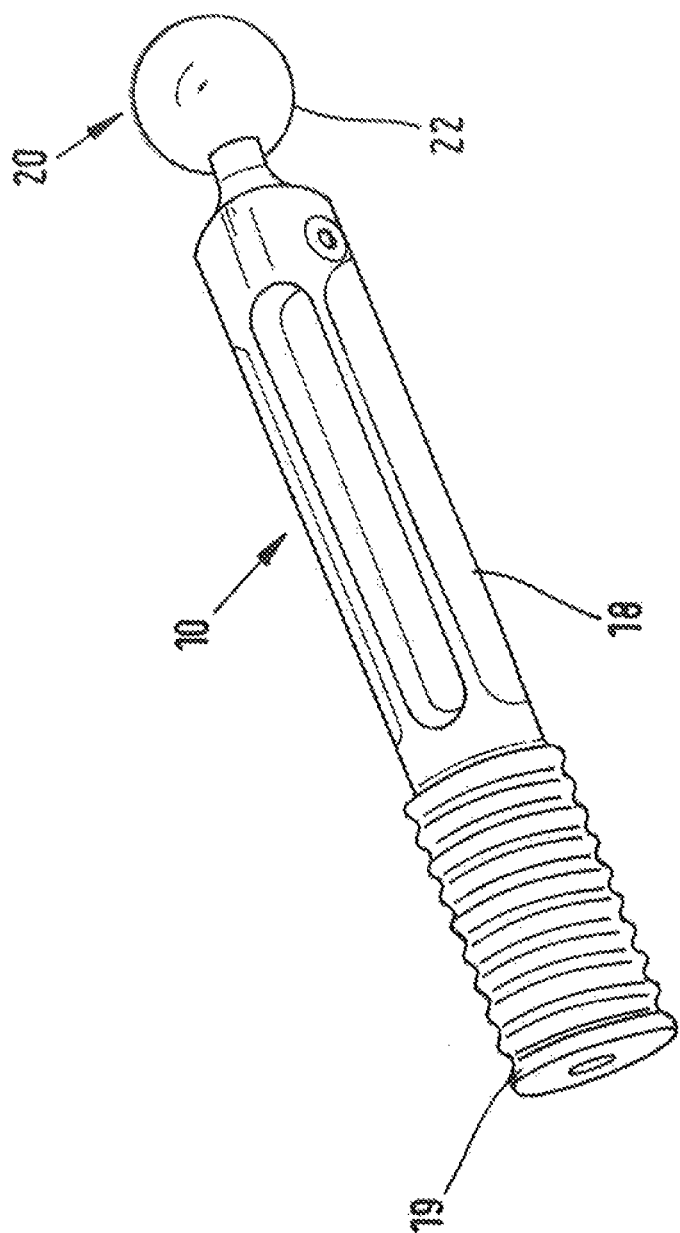
FIG. 4 is a perspective view of an embodiment of a handle.

Referring to FIG. 4, the handles 10 illustrated in FIGS. 1 to 3 will now be described in more detail. As shown, a ball joint member 22 is disposed on a distal end 20 of each handle 10. When the surgical assembly 200 is assembled, the ball joint member 22 is disposed within the surgical clamping device 100 co-operate with the surgical clamping device 100. The handle 10 has a hand grip 18 thereon to aid an operator in gripping the handle 10. Further, a connection portion 19 located on a proximal end of the handle 10 is adapted to connect to a distal end of one of the connector adaptors 23.

The surgical clamping device 100 will now be described with respect to FIGS. 5A-B, 6, 7, 8A-B, 9 and 10, which show the surgical clamping device 100 in greater detail.

Figure 5A:
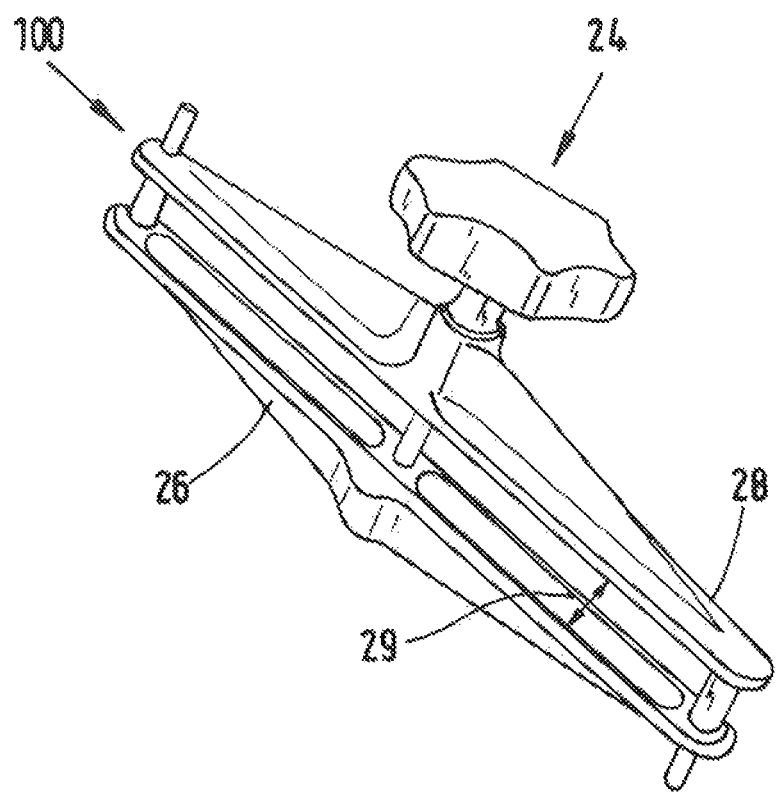
FIG. 5A is a perspective view showing an embodiment of a surgical clamping device.
Figure 5B:
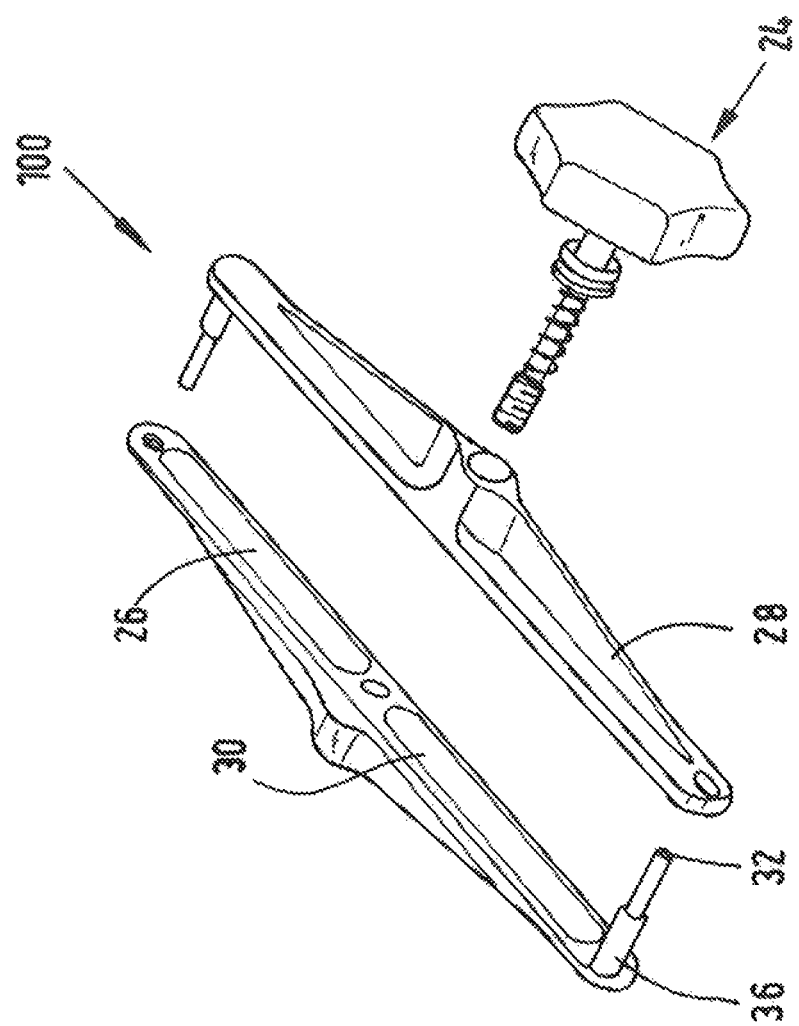
FIG. 5B is an exploded view showing the surgical clamping device of FIG. 5A.

FIG. 5A shows the surgical clamping device in an assembled state, but without the ball joint members 22 disposed in the surgical clamping device 100, and FIG. 5B shows an exploded view of the surgical clamping device 100 assembly of FIG. 5A. As illustrated in FIGS. 5A and 5B, the surgical clamping device 100 comprises two clamping members 26, 28 in the form of clamping plates, or rails, disposed opposite to each other. The clamping members 26, 28 are identical components disposed in an opposing symmetrical manner. The clamping members 26, 28 define a recess 29 between them which is adapted to receive the ball joint members 22 disposed on the distal ends 20 of the handles 10.

The recess 29 is defined by grooves 30 disposed on inner surfaces of the clamping members 26, 28 on the one hand and, on the other hand, by a free space defined by spacer portions 36 disposed on coupling members 32 located in coupling holes 34. The spacer portions 36 are adapted to maintain a minimum distance between the clamping members 26, 28 such that the assembly of the clamping members 26, 28 around the ball joint members 22 is facilitated.

The curvature of the grooves 30 is generally matched to the curvature of the ball joint members 22, so that the grooves 30 can function in a ball cup manner as regards a pivotal or rotating movement of the ball joint members, and additionally provide an axial guidance upon an axial movement of the ball joint members 22. For instance, to facilitate movement of the ball joint members 22 the inner curvature of the grooves 30 may be slightly larger than the curvature of the ball joint members 22.

Figure 6:
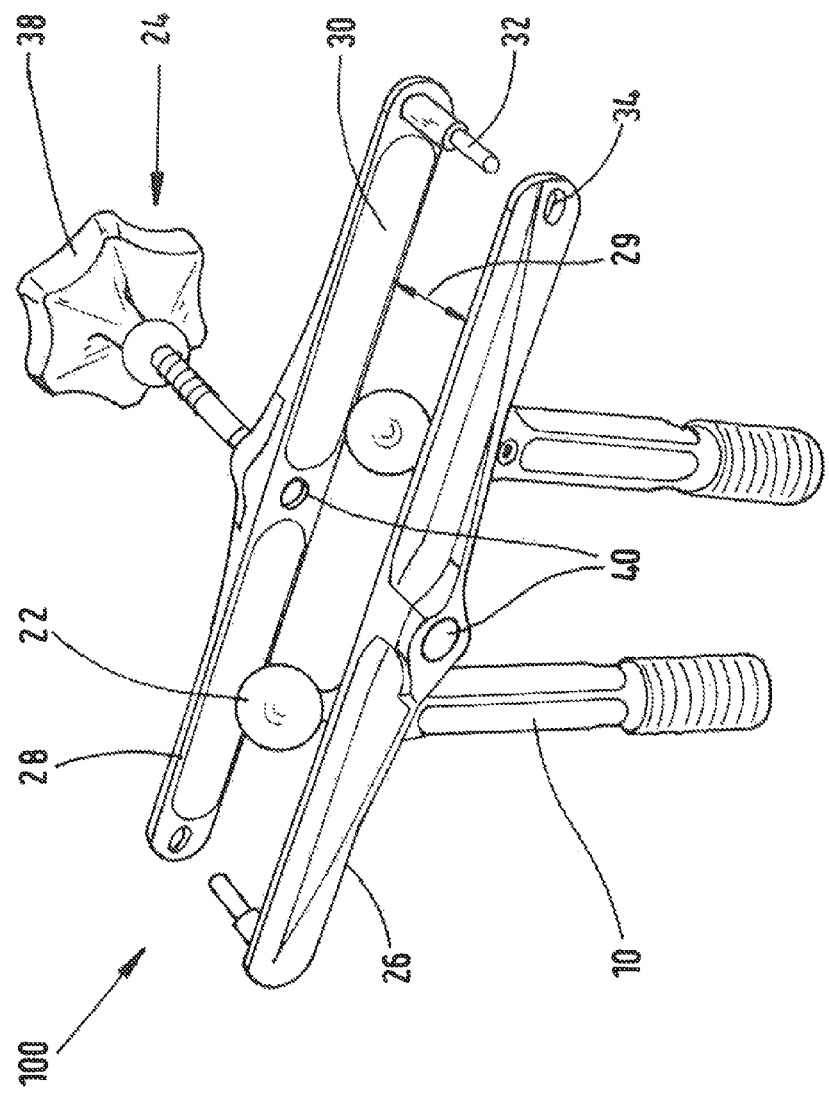
FIG. 6 is an exploded view of an embodiment of a surgical subassembly.

The coupling members 32 are disposed in the coupling holes 34 of the clamping members 26, 28 as shown in more detail in FIG. 6. The coupling holes 34 are elongated in the axial direction of the clamping members 26, 28. The coupling members 32 are adapted to maintain the two clamping members 26, 28 in axial and rotational alignment at least in the second, i.e., clamped state of the clamping members 26, 28. However, in the first, i.e., released state the coupling members 32 are loosely accommodated within the coupling holes 34 to allow the clamping members 26, 28 to be pivotally moved such that a distance between respective opposing ends of the clamping members 26, 28 may become larger or smaller (as indicated by the alignment lines illustrated in FIG. 10). Because the clamping members 26, 28 can move in this way, the assembly step of inserting the ball joint members 22 into the surgical clamping device 100 will become easier for the operator, since the distance between the clamping members 26, 28 may be widened at a desired insertion position for the ball joint members 22.

An adjusting mechanism 24, which will be described further with respect to FIGS. 6, 7, 8A-8B, 9 and 10, is disposed on the clamping members 26, 28 by being inserted through adjusting mechanism receiving holes 40, which are located approximately in the center of the clamping members 26, 28.

Figure 7:
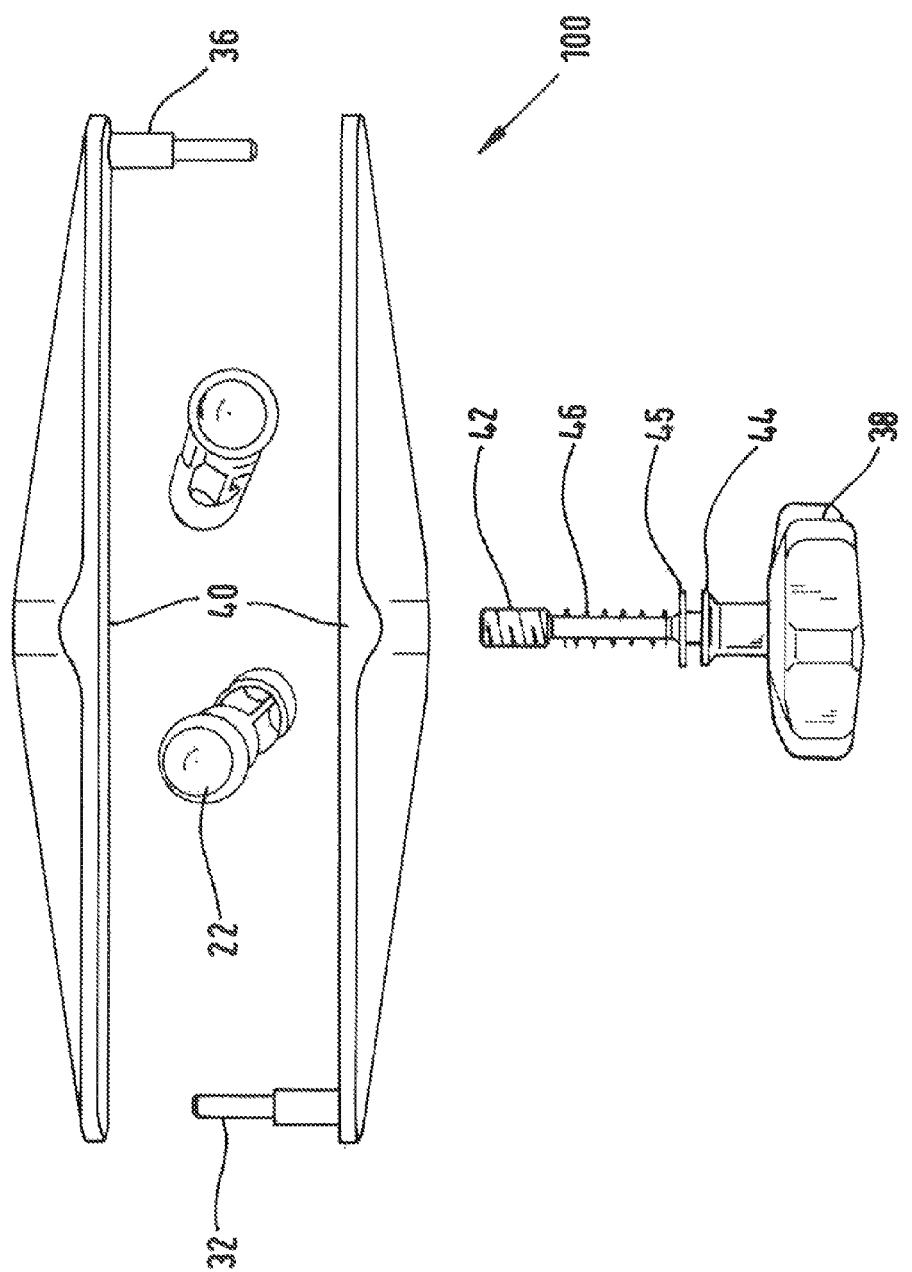
FIG. 7 is a second exploded view of the surgical subassembly of FIG. 6.
Figure 8B:
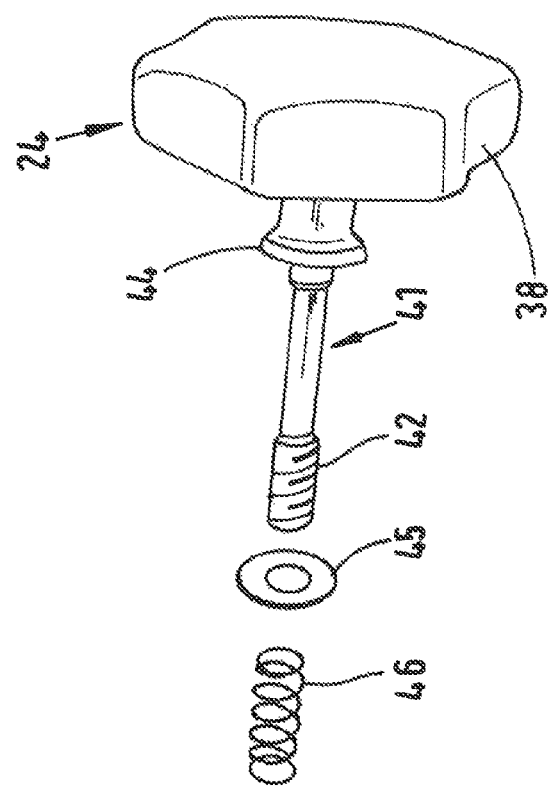
FIG. 8B is an exploded view of the attachment member of FIG. 8A.
Figure 8A:
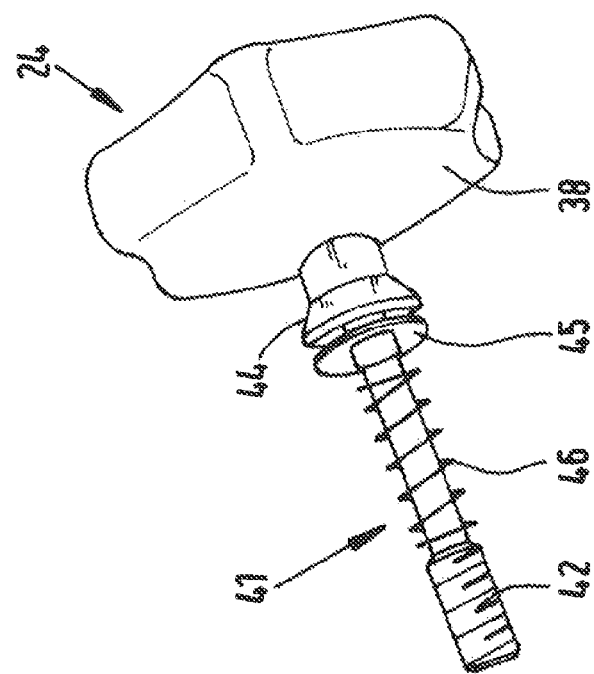
FIG. 8A is a perspective view of an embodiment of an attachment member.

The adjusting mechanism 24 comprises a compression screw with a shaft 41 and a threaded portion 42, shown with respect to FIG. 7, adapted to engage a threaded portion of the adjusting mechanism receiving holes 40 of the clamping members 26, 28. The shaft 41 has a smaller diameter than that of the threaded portion 42. Thereby, the shaft 41 of the adjusting member 24 is allowed to pivot slightly within the adjusting member receiving hole 40, as described below with respect to FIGS. 9 and 10.

Further, the adjusting mechanism 24 comprises a handle member 38 for receiving an input force from the operator to change a state of the surgical clamping device 100 from the released state (first state) to the clamped state (second state), and vice versa. The handle member 38 comprises a knob that may be turned by the operator.

Between an outer surface of the clamping member 26 and an inner surface of a rim 44 next to the handle member 38, an elastic member 46, such as a spring, is disposed on the shaft 41 (see FIGS. 7, 8A, 8B and 9). Further, an optional antifriction washer 45 is disposed between the rim 44 and the elastic member 46. The elastic member 46 urges the clamping members 26, 28 toward each other to hold the ball joint members 22 in the recess 29 in the first, i.e., released state. In one example, the elastic member 46 and the washer 45 are prevented from sliding off the adjusting member 24 by the relatively smaller diameter of the shaft 41 in relation to the threaded portion 42.

Figure 9:
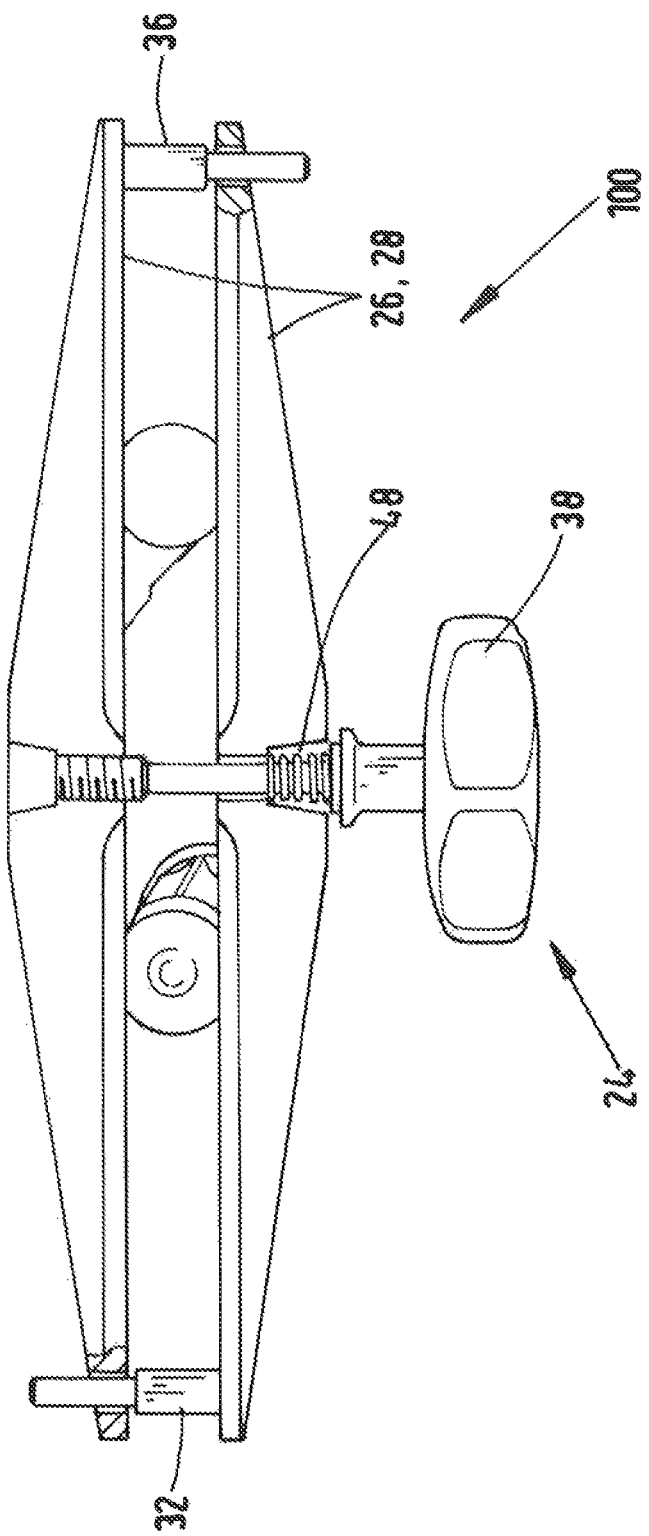
FIG. 9 is a view of the surgical subassembly of FIG. 7.

With respect to FIG. 9, when the adjusting mechanism 24 is inserted into the adjusting mechanism receiving holes 40 of the clamping members 26, 28, the coupling between the threaded portion of the adjusting mechanism receiving hole 40 and the threaded portion 42 of the adjusting mechanism 40 determines the distance between the clamping members 26, 28 at the position of the adjusting mechanism receiving holes 40.

In order to insert or remove the ball joint members 22 from the clamping device 100 in the first state, the clamping members 26, 28 may be manually dragged away from each other against the elastic force of the elastic member 46. As another example, the operator may apply a compressive force to one end of the surgical clamping assembly 100, thereby widening the distance between the clamping members 26, 28 at the opposite end, as shown with respect to FIG. 10.

Figure 10:
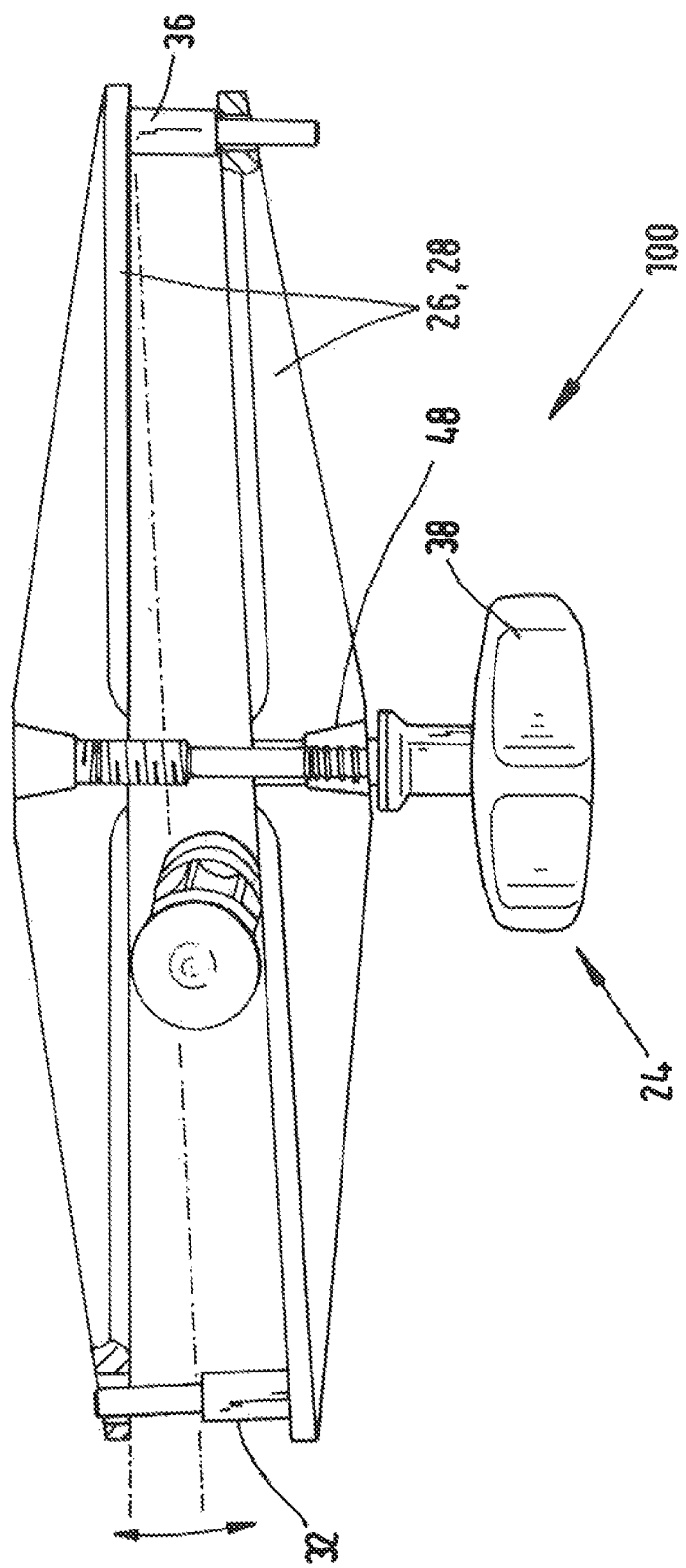
FIG. 10 is another view of the surgical subassembly of FIG. 7.

With further reference to FIG. 10, an outer portion of the adjusting mechanism receiving hole 40 comprises a tapered portion 48. The tapered portion 48 may have a conical shape. The tapered portion 48 allows the adjusting mechanism 24 to pivot such that an angle between the adjusting member 24 and the clamping member 28 is changed. At the same time, the tapered portion 48 defines a range of pivotal movement between the clamping members 26, 28. The surgical clamping device 100 can thus be actuated such that the clamping members 26, 28 are not parallel to each other (i.e., such that a larger displacement between the clamping members 26, 28 exists at a first side of the surgical clamping assembly 200 than at an opposite side of the surgical clamping assembly 200, as shown, for example, by alignment lines in FIG. 10). Thereby, the assembly of the ball joint members 22 into the recess 29 formed by the grooves 30 of the clamping members 26, 28 is facilitated.

Further, when the surgical clamping device 200 is assembled and the adjusting mechanism 24 is disposed in the adjusting member receiving holes 40 of both clamping members 26, 28 such that the elastic member 46 is compressed, and, consequently, expanded in a radial direction of the adjusting member 24, the tapered portion 48 provides a clearance space such that the elastic member 24 does not contact the adjusting member receiving hole 40. Thereby, damage to the elastic member 24 and the adjusting mechanism receiving hole 40 can be prevented.

Figure 11:
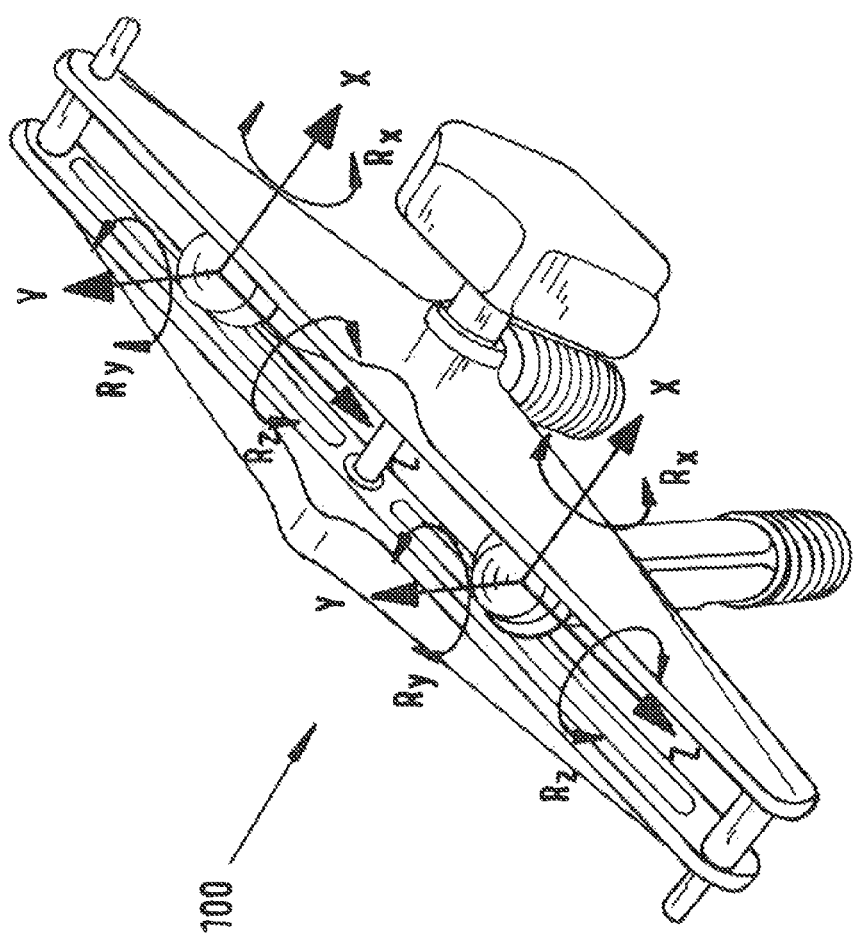
FIG. 11 is still further a perspective view of the surgical subassembly of FIG. 7.

With reference again to FIG. 9, when the ball joint members 22 are disposed in the recess 29, each ball joint member 22 is moveably supported by the grooves 30 of the clamping members 26, 28 in the first state, such that the ball joint members 22 cannot be removed from the surgical clamping device 100 without further widening of the distance between the clamping members 26, 28. With respect to FIG. 11, when the surgical clamping device 100 is in the first state, the ball joint members 22 have freedom of movement such that the ball joint members 22 can move axially in the Z direction as indicated in FIG. 11, and can pivot (or rotate) around the X, Y, and Z axes. Axial movement in the X and Y direction is restricted by the grooves 30 of the clamping members 26, 28. Further, the operator is able to cross the handles 10 within the surgical clamping device 100 in the first state.

The distance between the clamping members 26, 28 in the first state is determined by the adjusting mechanism 24. By operating the handle member 38 to change the position of the threaded portion 42 of the adjusting mechanism 24 in relation to the second clamping member 28 when the surgical clamping device 100 is in the first, released state, the distance between the two clamping members 26, 28 can be decreased and the clamping force exerted on the ball joint member 22 is increased.

When the handle member 38 has been operated such that the clamping force exerted on the ball joint member 22 is sufficient to prevent the ball joint members 22 from moving axially and rotationally and from pivoting within the grooves 30, the surgical clamping device 100 has entered the second, clamped state. When the surgical clamping device 100 is in the second state, the ball joint members 22 are fixed by the clamping force from the clamping members 26, 28. Therefore, the ball joint members 22 are prevented from axial movement, pivotal and rotational movement in the X, Y, and Z directions. In other words, the second state of surgical clamping device 100 provides a secure fixation of the handles 10, the connector adaptors 23, and the bone attachment members 14.

In the following the assembling of the surgical clamping device 100 is described with regard to FIGS. 6 and 9-11. Initially, the two clamping members 26, 28 are disposed opposite to each other, with their surfaces comprising the grooves 30 facing each other as shown in FIG. 6. In a next step, the adjusting mechanism 24 having the elastic member 46 and the washer 44 disposed thereon is inserted through the adjusting mechanism receiving hole 40 of the first clamping member 28. Further, the coupling members 32 are inserted into the coupling holes 34.

The threaded portion 42 of the adjusting mechanism 24 is then inserted into the adjusting mechanism receiving hole 40 of the second clamping member 26. To this end, the handle member 38 is actuated to engage the threaded portion 42 of the compression screw with the threaded portion of the adjusting mechanism receiving hole 40 in the second clamping member 26.

In a further step, the distance between the clamping members 26, 28 is manually expanded against the elastic force of the elastic member 46 to insert the ball joint members 22 of the handles into the recess 29. As described above with respect to FIG. 10, the space between the clamping members 26, 28 may also be widened by applying a compressing force to the opposite side of the surgical clamping device 100 from the side into which the ball joint 22 is being inserted. Alternatively, the distance between the clamping members 26, 28 may be expanded by the ball join member 22 being pushed into the recess 30 between the clamping members 26, 28.

The adjusting mechanism 24 may then be adjusted to bring the clamping members 26, 28 to a position in which the ball joint members 22 are securely held within the grooves 30, but are still able to rotate and move axially, and to pivot within the grooves 30 (this corresponds to the first, released state of the adjusting mechanism 42). The distractor 12 may have already earlier been disposed near the proximal ends of the connector adaptors 23 as generally shown in FIG. 1.

Having described the configuration and assembling the of surgical clamping device 100 and of the surgical assembly 200, the operation of the above-described surgical assembly 200 will now be described with reference to an exemplary dekyphosis procedure. It will be appreciated that the surgical assembly 200 can also be used in other procedures that involve the treatment of bone structures.

After preparing the patient site, the operator inserts the bone attachment members 14 into the vertebrae S selected for realignment as generally shown in FIG. 3. The connector adaptors 23 are then coupled to the bone attachment members 14 by sliding the connector adaptors 23 over the bone attachment members 14 until proximal ends of the connector adaptors 23 reach a surface of the vertebrae S. The handles 10 are coupled to distal ends of the connector adaptors 23. Next, the surgical clamping device 100 is assembled around the ball joint members 22 of the handles 10 as described above with respect to FIGS. 6 and 9-11.

The distractor 12 is positioned at or near proximal ends of the connector adaptors 23. Then, the operator grasps the hand grips 18 and moves the handles 10 to properly position the vertebrae S (see FIG. 1). For example, in the released state of the adjusting mechanism 24, the operator may pivot, rotate, or move the handles 10 axially within the grooves 30 of the surgical clamping device 100. Further, the operator is able to cross the handles 10 if desired. Also, the operator can adjust the distance between the proximal ends 16 of the handles 10 by adjusting the distractor 12.

When the operator has achieved the desired positioning of the vertebrae S, the operator adjusts the adjusting mechanism 24 by turning the handle member 38 to change the adjusting mechanism 24 from the first, released state into the second, clamped state. Thereby, the position of the ball joint members 22 is locked due to the clamping force of the surgical clamping device 100.

Next, the operator checks the alignment of the vertebrae S by taking an X-ray image of the surgical site. Before the X-ray image is taken, the operator exits the room or surgical site to avoid the harmful effects of exposure to X-ray radiation. Because the surgical clamping device 100 holds the positioning of the surgical clamping device 200 when the operator releases his grip on the surgical assembly 200, the positioning implemented by the operator can be preserved. Moreover, the surgical time may be reduced because the operator does not have to readjust the positioning of the vertebrae and the bone attachment members 14 after he releases the surgical assembly 200, and trauma to the patient caused by slipping of the surgical assembly 200 and bone attachment members 14, as well as increased risk to the patient caused by an extended surgery time, may be avoided.

If the operator determines after having analysed the X-ray images that the vertebral alignment needs to be readjusted, the operator can further adjust the adjusting mechanism 24 in the opposite direction to place the surgical clamping device 100 into the first, released state, in which the handles 10, ball joint members 22, and the bone attachment members 14 may be moved as desired by the operator.

Having described the preferred embodiments of the invention referring to the accompanying drawings, it should be understood that the present disclosure is not limited to those precise embodiments and various changes and modifications thereof could be made by one skilled in the art.

The invention claimed is:

1. A surgical assembly comprising at least one surgical clamping device and a plurality of handles, the at least one clamping device comprising:
    two opposing clamping members;
    at least one recess disposed in the surgical clamping device and adapted to receive distal ends of the plurality of handles having bone attachment members disposed thereon, wherein the recess is defined between the two clamping member, and wherein the recess comprises one or more grooves disposed on one of the clamping members or on opposing faces of the clamping members;
    an adjusting mechanism adapted to adjust the recess between a first state in which at least one of the distal ends of the plurality of handles is pivotable within the recess, wherein the distal ends of the plurality of handles are supported by the one or more grooves of the clamping members in the first state such that the distal ends cannot be removed from the recess without widening a distance between the clamping members, and a second state in which the distal ends of the handles are axially and pivotably fixed within the recess; and
    wherein the distal end of each handle comprises a ball joint member adapted to pivot and to axially move within the recess in the first state, and adapted to be fixed within the recess in the second state.

2. The surgical assembly of claim 1, further comprising an adjusting mechanism receiving portion disposed on at least one of the clamping members, wherein, when the adjusting mechanism is adjusted, the position of the adjusting mechanism receiving portion in relation to the adjusting mechanism is changed, thereby changing a distance between the two clamping members.

3. The surgical assembly of claim 2, wherein the adjusting mechanism comprises a compression screw having a threaded portion and a handle member coupled to the compression screw, and wherein the adjusting mechanism receiving portion comprises a threaded portion adapted to receive the threaded portion of the compression screw.

4. The surgical assembly of claim 3, wherein, when the handle member is operated, the threaded portion of the adjusting mechanism receiving portion couples with the threaded portion of the compression screw to move the adjusting mechanism in relation to the adjusting mechanism receiving portion, thereby changing the distance between the clamping members.

5. The surgical assembly of claim 3 further comprising an elastic member disposed between a surface of one of the two clamping members and the adjusting mechanism, and adapted to urge the one clamping member towards the opposed clamping member, wherein the elastic member is disposed between the surface of the one clamping member and a rim of the adjusting mechanism.

6. The surgical assembly of claim 3, further comprising a tapered portion disposed in the adjusting member receiving portion, the tapered position defining a range of pivotal movement between the clamping members.

7. The surgical assembly of claim 1, further comprising an elastic member disposed between a surface of one of the clamping members and the adjusting mechanism, the elastic member adapted to urge the one clamping member towards the opposed clamping member.

8. The surgical assembly of claim 1, further comprising one or more coupling members at least partially disposed between the clamping members and adapted to axially and rotationally align the clamping members.

9. The surgical assembly of claim 8, wherein the one or more coupling members further comprise spacer portions adapted to maintain a minimum space between the clamping members.

10. The surgical assembly of claim 8, wherein the clamping members comprises two elongated coupling holes at opposite ends thereof for pivotally receiving the coupling members.

11. The surgical assembly of claim 1 wherein the bone attachment members are disposed on the proximal ends of the plurality of handles.

12. The surgical assembly of claim 1, wherein a connector adaptor is disposed between the bone attachment members and the handles.

13. The surgical assembly of claim 1, further comprising a distractor coupled to proximal portions of at least two connector adaptors and adapted to fix the bone attachment members at a selected distance from each other.

14. A surgical assembly comprising:
a clamping device comprising first and second juxtaposed clamping plates having facing surfaces, each facing surface having a curved groove extending along a first axis of the first clamping plate and along a second axis of the second clamping plate, a first and second alignment element engaging each clamping plate for maintaining the first axis along the first clamping plate parallel to the second axis along the second clamping plate, the first clamping plate having a threaded bore therein and the second clamping plate having a tapered bore therein, the threaded bore and tapered bore both extending along a third axis transverse to the first and second axis;
a pair of handle members each having a ball-shaped head mounted within the curved groove of the first and second clamping plates; and
an adjusting mechanism having a shaft received within the threaded and tapered bores of the first and second clamping plates, the adjusting mechanism shaft including a threaded end operatively engaging the threaded bore of the first clamping plate and an elastic member mounted on the shaft engaging the second clamping plate the adjustment mechanism capable of moving the first and second clamping plates towards one another.

15. The surgical assembly as set forth in claim 14 wherein the elastic element is a coil spring mounted on a shaft portion located at least partially within the tapered bore of the second clamping member.

16. The surgical assembly as set forth in claim 14 wherein the shaft has an end having a drive member mounted thereon for rotating the shaft of the adjusting mechanism.

17. The surgical assembly as set forth in claim 16 wherein rotation of the drive member in a first direction moves the facing surfaces of the first and second clamping plates towards each other.

18. The surgical assembly as set forth in claim 17 wherein the first and second alignment elements extend between the facing surfaces of the first and second clamping plates and each include a stop surface engagable with one of the first and second clamping plates to maintain a minimum distance between the facing surfaces.

19. The surgical assembly as set forth in claim 14 wherein the tapered bore of the second clamping element defines a range of pivotal movement between the first and second clamping plates.

* * * * *